United States Patent [19]

Watkins

[11] Patent Number: 5,182,264
[45] Date of Patent: Jan. 26, 1993

[54] ANGIOTENSIN II RECEPTOR BLOCKERS AS ANTIGLAUCOMA AGENTS

[75] Inventor: Robert W. Watkins, Great Meadows, N.J.

[73] Assignee: Schering Corporation, Kenilworth, N.J.

[21] Appl. No.: 696,374

[22] Filed: May 6, 1991

Related U.S. Application Data

[62] Division of Ser. No. 837,452, Mar. 7, 1986, Pat. No. 5,036,048.

[51] Int. Cl.$^5$ .................. A61K 31/475; A61K 31/13; A61K 31/54
[52] U.S. Cl. .................................. 514/16; 514/17; 514/15; 514/912; 422/61; 435/810; 436/808
[58] Field of Search ................. 514/16, 17, 15, 912; 435/810; 436/808; 422/61

[56] References Cited

U.S. PATENT DOCUMENTS

| | | | |
|---|---|---|---|
| 3,571,404 | 8/1973 | Sipos et al. | 530/316 |
| 3,886,134 | 5/1975 | Sipos et al. | 530/316 |
| 3,907,762 | 9/1975 | Regoli et al. | 530/316 |
| 3,915,948 | 10/1975 | Wille | 530/316 |
| 3,923,769 | 12/1975 | Bumpus et al. | 530/316 |
| 3,923,770 | 12/1975 | Bumpus et al. | 530/316 |
| 3,923,771 | 12/1975 | Bumpus et al. | 530/316 |
| 3,925,345 | 12/1975 | Bumpus et al. | 530/316 |
| 3,932,624 | 1/1976 | Fulton | 514/16 |
| 3,976,770 | 8/1976 | Bumpus et al. | |
| 4,013,791 | 3/1977 | Wissman et al. | 530/316 |
| 4,179,433 | 12/1979 | Kisfaludy et al. | 514/316 |
| 4,204,991 | 5/1980 | Hallinan et al. | 530/316 |
| 4,209,442 | 6/1980 | Kisfaludy et al. | 530/316 |
| 4,330,532 | 5/1982 | Nyeki et al. | 530/316 |
| 4,340,598 | 7/1982 | Furukawa et al. | 514/400 |
| 4,355,040 | 11/1982 | Furukawa et al. | 514/400 |
| 4,388,304 | 6/1983 | Nyeki et al. | 530/316 |
| 4,444,778 | 4/1984 | Coughlin | 514/280 |
| 4,515,800 | 5/1985 | Cavero et al. | 514/392 |
| 4,517,199 | 5/1985 | York, Jr. | 514/392 |
| 4,616,012 | 10/1986 | Neustadt et al. | 514/222 |
| 5,036,048 | 7/1991 | Watkins | 514/16 |

FOREIGN PATENT DOCUMENTS

| | | |
|---|---|---|
| 34259 | 8/1981 | European Pat. Off. |
| 36351 | 9/1981 | European Pat. Off. |
| 0105996 | 4/1984 | European Pat. Off. |
| 0118940 | 9/1984 | European Pat. Off. |
| 2520106 | 5/1975 | Fed. Rep. of Germany |
| 891648 | 12/1981 | U.S.S.R. |

OTHER PUBLICATIONS

Chem. Abstract, vol. 91, 1979, abstract 91:74909d.
Clinical Science and Molecular Medicine, (1976), 51, 403s–406s.
Ionistescu C., Rev. Chir., (oftalmol.), 26(2), 137–138 (with English translation).
The Merck Manual, 11th Edition, Rahway, N.J., 1966, pp. 484 and 511–515.
Stedman's Medical Dictionary, 22nd Edition; 1972, pp. 604, 643.
D. Regoli and J. R. Vane, A Sensitive Method for the Assay of Angiotension, Brit. J. Pharmacol., (1964), 23, pp. 351–359.
Remington's Pharmaceutical Sciences, Arthur Osol, (ed.), 16th Edition, Mack Publishing Co., Easton, Pa., 1980, p. 783.
Stedman's Medical Dictionary, 23rd Ed., The Williams & Wilkins Co., Baltimore, Md., 1976, pp. 586 and 203.
The Merck Index, 9th Ed., Merck & Co., Rahway, N.J., 1976, pp. 170 and 2899–2900.
Kul Bhushan Anand et al., Systemic Effects of Opthalmic Medication in the Elderly, Mar. 1988, pp. 134–136, New York State Journal of Medicine.
J. Cardivasc. Pharm., 5:1025, 1983.
Can. J. Physiol. Pharm., 57:763, 1979.
R. R. Luther et al., Renin Inhibitors: Specific Modulators of the Renin-Angiotensin System, Arzneim-Forsch./Drug Res., 39(1), No. 1, (1989), pp. 1–5.
Miguel A. Ondetti et al., Inhibition of the Renin-Angiotensin System. A New Approach to the Therapy of Hypertension, Journal of Medicinal Chemistry, vol. 24, No. 4, Apr. 1981, pp. 355–361.
Chiu et al., "Nonpeptide Angiotensin II Receptor Antagonists, VII. Cellular and Biochemical Pharmacology of DuP753, an Orally Active Antihypertensive Agent", *The Journal of Pharmacology and Experimental Therapeutics*, (1990), vol. 252, No. 2, pp. 711–718.
Wong et al., "Nonpetide Angiotensin II Receptor Antagonists, VIII. Characterization of Functional Antagonism Displayed by DuP753, and Orally Active Antihypertensive Agent", *The Journal of Pharmacology and Experimental Therapeutics*, (1990), vol. 252, No. 2, pp. 719–725.
Duncia et al., "The Discovery of Patent Nonpetide Angiotension II Receptor Antagonists: A New Class of Potent Antihypertensives", *J. Med. Chem.*, 1990, 33, pp. 1312–1329.
Carini et al., "Nonpeptide Angiotensin II Receptor Antagonists: N-[(Benzyloxy)benzyl] imidazoles and Related Compounds Potent Antipertensives", *J. Med. Chem.*, 1990, 33, pp. 1330–1336.
P. A. Khairallah et al., J. Med. Chem., 13, 181 (1970).
Clin. Sci., 57:71, 1979.
Endocrinology, 107(5):1305, 1980.
Am. Journal Physiol., 236(3):F252, 1976.

(List continued on next page.)

*Primary Examiner*—Ronald W. Griffin
*Attorney, Agent, or Firm*—Joseph T. Majka; James R. Nelson

[57] ABSTRACT

A method and composition for reducing and/or controlling elevated intraocular pressure, especially the elevated intraocular pressure associated with glaucoma, are disclosed in which an angiotensin II antagonist is administered to the eye.

25 Claims, No Drawings

OTHER PUBLICATIONS

Clin. Sci. Mol. Med., 51:385s, 1976.
Am. J. Physiol., 236(3):F252, 1976.
Clin. Sci. Mol. Med., 51:385s, 1976.
J. Cardiovasc. Pharm., 5:1025, 1983.
Life Sci., 34:317, 1983.
Can. J. Physiol. Pharm., 57:121, 1979.
J. Pharm. Pharmacol., 32:232, 1980.
J. Med. Chem., 22(9):1147, 1979.
J. Med. Chem., 20(2):253, 1977.
J. Med. Chem., 19(2):244, 1976.
J. Med. Chem., 13:181, 1970.
Circ. Res., 29:664, 1971.
Circ. Res., 46:720, 1980.
Proc. Nat'l Acad. Sci. U.S.A., 67:1624, 1970.
J. Med. Chem., 20:898, 1977.
Cir. Res., 31:862, 1972.
Chemical Abstracts, vol. 95, Abstract No. 175775V.
Chemical Abstracts, vol. 89, Abstract No. 24819n.
Chemical Abstracts, vol. 91, Abstract No. 39880r.
Chemical Abstracts, vol. 91, Abstract No. 74909d.
Chemical Abstracts, vol. 95, Abstract No. 7777d.
Weiner, N., The Pharmaceutical Basis of Therapeutics, (ed. A. G. Goodman, L. S. Goodman, A. Gilman), Macmillan Publishing, New York, 1980, 6th Ed., pp. 188–197.
Physicians Desk Reference for Opthalmology, 11th Ed., 1983, p. 126.

ANGIOTENSIN II RECEPTOR BLOCKERS AS ANTIGLAUCOMA AGENTS

This is a division of application Ser. No. 06/837,452 filed Mar. 7, 1986 now U.S. Pat. No. 5,036,048.

The present invention relates to ophthalmic pharmaceutical compositions comprising angiotensin II antagonists and to methods for using said compositions in the treatment of elevated intraocular pressure, especially that associated with glaucoma.

BACKGROUND OF THE INVENTION

Angiotensin II analogues which function as angiotensin II antagonists are useful in the diagnosis and treatment of mammalian hypertension were reported in G. R. Marshal et al., *Proc Nat. Acad Sci USA* 67, 1624 (1970) and P. A. Khairallah et. al., *J. Med Chem.* 13, 181 (1970). U.S. Pat. Nos. 3,751,404, 3,886,134, 3,907,762, 3,915,948, 3,923,769, 3,923,770, 3,923,771, 3,925,345, 3,976,770, 4,013,791, 4,179,433, 4,204,991, 4,209,442 and 4,330,532 disclose derivatized peptides incorporating portions of the amino acid sequence of angiotensin II. U.S. Pat. Nos. 4,340,598 and 4,355,040 disclose imidazole derivatives reported to be antagonistic to angiotensin II. The use of angiotensin II antagonists in the treatment of elevated intraocular pressure has not been disclosed.

Glaucoma is an ocular disease complex associated with an elevated pressure within the eye (i.e., intraocular pressure, IOP). As a result of the elevated IOP, damage to the optic nerve resulting in irreversible loss of visual function may ensue. Untreated, this condition may eventually lead to blindness.

Ocular hypertension, i.e., a condition of elevated intraocular pressure without optic nerve damage or characteristic glaucomatous visual field loss, is now believed by the majority of ophthalmologists to represent the earliest phase in the onset of glaucoma.

A number of the drugs presently employed to treat glaucoma are not entirely satisfactory, particularly in the earliest course of the disease when the side effects they produce are often worse than the symptoms of the disease.

Epinephrine, used as a topical solution, must be utilized cautiously in patients with high blood pressure, diabetes, hyperthyroidism and cerebral arteriosclerosis due to the possibility of systemic action.

Timolol, a clinically utilized, topically applied agent for lowering IOP, must be used with caution in patients in whom beta-adrenergic blockade may be undesirable. Systemic absorption of topically administered timolol and the resulting systemic beta-blockade are responsible for the contraindication of timolol therapy in glaucoma patients with compromised pulmonary function and in patients who cannot tolerate its systemic cardiovascular actions.

Pilocarpine, a topical drug, although considered systemically harmless and quite effective, may cause considerable local difficulties. Pupil constriction causes the eye to lose its ability to adapt from light to dark. Accommodation may become so stimulated that the patient's refraction is sometimes incorrect and vision becomes blurred. The drug itself may cause a local vasodilation and red eyes. Irritation is common.

Carbonic anhydrase antagonists have been used systemically but they have a number of disadvantages. While effective in lowering intraocular pressure, they often cause a numbness and tingling, gastrointestinal upsets and, frequently, depression, lethargy, a loss of appetite, and general malaise. European Patent Application 81400326.5, Publication number 36,351, attempts to overcome these difficulties by the topical administration of an alkali metal salt of a carbonic anhydrase antagonist.

The present invention provides a new method for reducing and controlling elevated IOP, especially the elevated IOP associated with glaucoma.

SUMMARY OF THE INVENTION

The present invention includes a method for reducing and controlling elevated intraocular pressure (IOP), especially the elevated intraocular pressure associated with glaucoma, in a mammal which comprises topically administering an intraocular pressure reducing effective amount of an angiotensin II antagonist to an eye of said mammal. A pharmaceutical composition comprising an angiotensin II antagonist in combination with an ophthalmically acceptable carrier for topical use can be employed for this purpose. Such method and composition may also be used in conjunction with the administration of a beta-adrenergic blocking agent and/or an anti-inflammatory steroid.

The invention in another aspect involves two kits for use in reducing and controlling elevated intraocular pressure. The kits comprises first and second containers, in a single package. The first container in both kits includes a topical pharmaceutical composition comprising an IOP reducing effective amount of an angiotensin II antagonist. In a first kit, the second container includes a pharmaceutical composition comprising an anti-inflammatory effective amount of a steroid in a pharmaceutically acceptable carrier. In a second kit, the second container includes a pharmaceutical composition comprising an intraocular presence reducing amount of beta adrenergic blocking agent in combination with an ophthamologically acceptable carrier for topical use.

DETAILED DESCRIPTION OF THE INVENTION

Angiotensin II is a polypeptide having, in man, the amino acid sequence Asp-Arg-Val-Tyr-Ile-His-Pro-Phe. (The abbreviations used herein are those published by the IUPAC-IUB Commission on Biochemical Nomenclature, *Archives of Biochemistry and Biophysics* 150, 1 (1972). The sequence is read N-terminus to carboxyl terminus. Unless otherwise indicated, the L stereochemical configuration is intended.) Some variation of this sequence, particularly at the fifth amino acid, may occur in lower animals. Angiotensin II (or AII) is a pressor substance formed from a decapeptide, angiotensin I, by the action of angiotensin converting enzyme (ACE). Angiotensin II is believed to exert its effect by interaction with a receptor. An angiotensin II antagonist, also known as an angiotensin II receptor blocker, prevents angiotensin II from exerting its effect, presumably by preventing interaction of angiotensin II with its receptor site.

Many angiotensin II antagonists are structurally analogous to angiotensin II. These compounds are, typically, derivatives of angiotensin II in which the N or carboxyl terminal amino acids have been replaced or derivatized. Replacement of selected internal amino acids, usually in conjunction with alteration of a terminal amino acid, has also been reported to be effective.

Examples of suitable angiotensin II antagonists include, but are not limited to, the following substances which are disclosed in the indicated publications:

| AII Analog* | Reference Citing AII Receptor Blocking Activity |
|---|---|
| Sar$^1$Ala$^8$ | Clin. Sci. 57: 71, 1979 |
| Sar$^1$ Ile$^8$ | Endocrinology 107(5): 1305, 1980 |
| Succ$^1$ Val$^5$ Phenylgly$^8$ | Clin. Sci. Mol. Med. 51: 4305, 1976 |
| desAsp$^1$ Ile$^8$ | Am J. Physiol. 236(3): F252, 1976 |
| Sar$^1$ Thr$^8$ | Clin. Sci. Mol. Med. 51: 3855, 1976 |
| Sar$^1$ Cys—Me$^8$ | J. Cardiovasc. Pharm. 5: 1025, 1983 |
| Sar$^1$ Tyr—Me$^4$ | Life Sci. 34: 317, 1983 |
| Gly$^8$ | Can J. Physiol Pharm. 57: 121, 1979 |
| Ile$^8$ | Can J. Physiol Pharm. 57: 121, 1979 |
| Leu$^8$ | Can J. Physiol Pharm. 57: 121, 1979 |
| Sar$^1$ Leu$^8$ | Can J. Physiol Pharm. 57: 121, 1979 |
| desAsp$^1$ Leu$^8$ | Can J. Physiol Pharm. 57: 121, 1979 |
| Sar$^1$ Me—Ala$^7$ Ile$^8$ | Can J. Physiol Pharm. 57: 763, 1979 |
| Sar$^1$ DL-Nipecotamide$^7$ Ile$^8$ | Can J. Physiol Pharm. 57: 763, 1979 |
| Sar$^1$ Sar$^7$ Ile$^8$ | Can J. Physiol Pharm. 57: 763, 1979 |
| 8-L—Ala | J. Pharm. Pharmacol. 32: 232, 1980 |
| Met$^8$ | J. Med. Chem. 22(9): 1147, 1979 |
| Thr$^8$ | J. Med. Chem. 22(9): 1147, 1979 |
| O—Me Thr$^8$ | J. Med. Chem. 22(9): 1147, 1979 |
| N—Me Ile$^8$ | J. Med. Chem. 22(9): 1147, 1979 |
| N—Me Phe$^8$ | J. Med. Chem. 22(9): 1147, 1979 |
| Sar$^1$ Sar$^7$ Leu$^8$ | J. Med. Chem. 22(9): 1147, 1979 |
| Sar$^1$ Sar$^7$ Thr(Me)$^8$ | J. Med. Chem. 22(9): 1147, 1979 |
| Sar$^1$ Sar$^7$ DLaIle$^8$ | J. Med. Chem. 22(9): 1147, 1979 |
| MeIle$^1$ Thr$^8$ | J. Med. Chem. 20(2): 253, 1977 |
| Me$_2$Gly$^1$ Thr$^8$ | J. Med. Chem. 20(2): 253, 1977 |
| GdnAc$^1$ Thr$^8$ | J. Med. Chem. 20(2): 253, 1977 |
| desAsp$^1$ Thr$^8$ | J. Med. Chem. 20(2): 253, 1977 |
| Sar$^1$ Ser(Me)$^8$ | J. Med. Chem. 20(2): 253, 1977 |
| Sar$^1$ Thr$^8$ | J. Med. Chem. 20(2): 253, 1977 |
| Sar$^1$ Thr(Me)$^8$ | J. Med. Chem. 19(2): 244, 1976 |
| MeAspNH$_2^1$ Ile$^8$ | J. Med. Chem. 19(2): 244, 1976 |
| Sar$^1$ MeTyr$^4$ Ile$^8$ | J. Med. Chem. 19(2): 244, 1976 |
| Sar$^1$ MeIle$^5$ Ile$^8$ | J. Med. Chem. 19(2): 244, 1976 |
| Sar$^1$ MeIle$^8$ | J. Med. Chem. 19(2): 244, 1976 |
| Sar$^1$ MeIle$^5$ MeIle$^8$ | J. Med. Chem. 19(2): 244, 1976 |
| Sar$^1$ Thr (O-$\beta$-Me)$^8$ | J. Med. Chem. 19(2): 244, 1976 |
| Sar$^1$ Met$^8$ | J. Med. Chem. 19(2): 244, 1976 |
| Sar$^1$ Ser$^8$ | J. Med. Chem. 19(2): 244, 1976 |
| Ile$^5$ Ala$^8$ | J. Med. Chem. 13: 181, 1970 |
| Ile$^5$, 8-(3-amino-4-phenyl)butyric acid | J. Med. Chem. 13: 181, 1970 |
| Asn$^1$ Ala$^8$ | Circ. Res. 29: 664, 1971 |
| Sar$^1$ Cys(Me)$^8$ | Circ. Res. 46: 720, 1980 |
| Phe$^4$ Tyr$^8$ | Proc. Nat'l Acad. Sci. USA 67: 1624, 1970 |
| OctanoylLeu$^8$ | J. Med. Chem. 20: 898, 1977 |
| Cys$^8$ | Cir. Res. 31: 862, 1972 |
| Phe$^4$ Tyr$^8$ | Cir. Res. 31: 862, 1972 |
| desAsp$^1$ Phe$^4$ Tyr$^8$ | Cir. Res. 31: 862, 1972 |
| para-fluoroPhe$^4$ | Cir. Res. 31: 862, 1972 |
| para-fluoroPhe$^8$ | Cir. Res. 31: 862, 1972 |

*Abbreviations indicate substitutions in the Angiotensin II (AII) sequence Asp—Arg—Val—Tyr—Ile—His—Pro—Phe with the location of the substitution identified by the superscript.

Another class of AII antagonists are disclosed in Sipos et al. U.S. Pat. No. 3,751,404 as having the formula

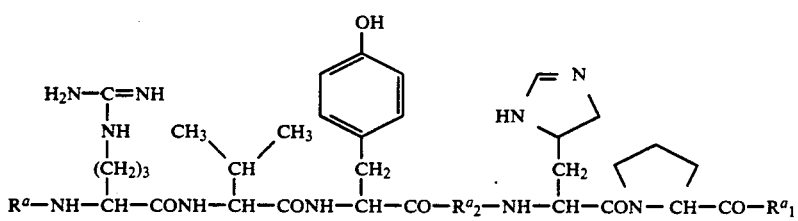

wherein R$^a$ is hydrogen, succinyl, L-aspartyl, sarcosyl, L-acryl, succinamyl, L-prolyl, glycyl, or D- or L-aspraginyl; R$^a_1$ is an L-alanine, L- or D-leucine, glycine, L-isoleucine or $\beta$-alanine residue; and R$^a_2$ is L-valyl, or L-alanyl.

Examples of suitable compounds within this class are
D-Asn-Arg-Val-Tyr-Val-His-Pro-Ala-OH
Asn-Arg-Val-Tyr-Val-His-Pro-Leu-OH
D-Asn-Arg-Val-Tyr-Val-His-Pro-Leu-OH
Succinyl-Arg-Val-Tyr-Val-His-Pro-Ala-OH
Asp-Arg-Val-Tyr-Val-His-Pro-Ala-OH
Arg-Val-Tyr-Val-His-Pro-Ala-OH
Sar-Arg-Val-Tyr-His-Pro-Ala-OH
Ser-Arg-Val-Tyr-His-Pro-Ala-OH
Asn-Arg-Val-Tyr-Val-His-Pro-D-Leu-OH
Succinamyl-Arg-Val-Tyr-Val-His-Pro-Ala-OH
Asn-Arg-Val-Tyr-Val-His-Pro-Gly-OH
Asn-Arg-Val-Tyr-Val-His-Pro-Ile-OH
Sar-Arg-Val-Tyr-Val-His-Pro-Gly-OH
Pro-Arg-Val-Tyr-Val-His-Pro-Gly-OH
Asn-Arg-Val-Tyr-Val-His-Pro-Gly-OH
Sar-Arg-Val-Tyr-Val-His-Pro-$\beta$-Ala-OH
Asn-Arg-Val-Tyr-Val-His-Pro-$\beta$-Ala-OH
Gly-Arg-Val-Tyr-Val-His-Pro-Ala-OH
Sar-Arg-Val-Tyr-Ile-His-Pro-Leu-OH
Asn-Arg-Val-Tyr-Ile-His-Pro-Leu-OH
Sar-Arg-Val-Tyr-Ile-His-Pro-Ala-OH
Asn-Arg-Val-Tyr-Ile-His-Pro-Ala-OH
Asn-Arg-Val-Tyr-Val-His-Pro-Ala-OH
Asn-Arg-Val-Tyr-Ala-His-Pro-Ala-OH Particularly preferred is Sar-Arg-Val-Tyr-Val-His-Pro-$\beta$-Ala-OH which is also referred to as Saralasin.

Regoli et al. U.S. Pat. No. 3,907,762 discloses as AII antagonists compounds of the formula $$\overset{1}{\text{Asp}}-\overset{2}{\text{Arg}}-\overset{3}{\text{Val}}-\overset{4}{\text{Tyr}}-\overset{5}{\text{Ile}}-\overset{6}{\text{His}}-\overset{7}{\text{Pro}}-\overset{8}{R^b}$$

wherein
R$^b$ is Leu (leucine),
Ile (isoleucine),
Val (valine), or
$\alpha$-amino-n-But ($\alpha$-amino-n-butyric acid) and Asp is aspartyl, Arg is arginyl, Val is valyl, Tyr is tyrosyl, Ile is isoleucyl, His is histidyl and Pro is prolyl.

Examples of suitable compounds within this class are
Asp-Arg-Val-Tyr-Ile-His-Pro-Leu-OH,
Asp-Arg-Val-Tyr-Ile-His-Pro-Ile-OH,
Asp-Arg-Val-Tyr-Ile-His-Pro-Val-OH, and
Asp-Arg-Val-Tyr-Ile-His-Pro-$\alpha$-amino-n-butyric acid.

AII receptor inhibitory activity is disclosed in Nyeki et al. U.S. Pat. No. 4,388,304 for compounds of the formula $$X^c\text{-Arg-Val-Tyr-Ile-His-Pro-}Y^c\text{-OA}^c \tag{I$^c$}$$

wherein

X$^c$ stands for the acyl group of an N-methylamino acid, preferably sarcosyl group, or the acyl group of an aliphatic α-hydroxy- or α-aminooxycarboxylic acid, $Y^c$ is the residue of an aliphatic amino acid, and $A^c$ is a $C_{1-5}$ alkyl group.

The acid addition salts and complexes of the above peptides are also embraced by the scope of the invention.

Compounds disclosed include

Sar-Arg-Val-Tyr-Ile-His-Pro-Ile-methyl ester, and hydroxyacetyl-Arg-Val-Tyr-Ile-His-Pro-Thr-methyl ester.

The same or similar compounds are also disclosed in European Patent No. 34,259.

Sipos et al. U.S. Pat. No. 3,886,134 discloses compounds having AII antagonists activity of the formula

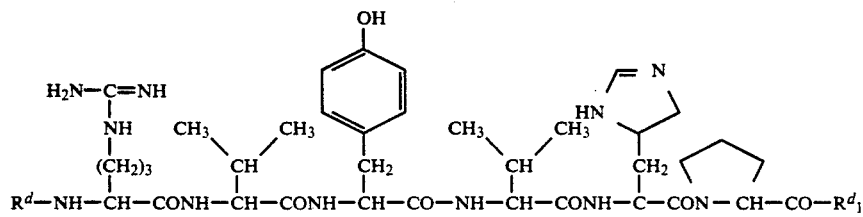

wherein $R^d$ is hydrogen, succinyl, L-aspartyl, sarcosyl, L-seryl, succinamyl, or D- or L-asparaginyl and $R_1^d$ is an L-alanine, L- or D-leucine, glycine or L-isoleucine residue.

Examples of compounds of this class are

Sar-Arg-Val-Tyr-Val-His-Pro-Ala-OH
Ser-Arg-Val-Tyr-Val-His-Pro-Ala-OH
Asn-Arg-Val-Tyr-Val-His-Pro-D-Leu-OH
Succinamyl-Arg-Val-Tyr-Val-His-Pro-Ala-OH
Arg-Val-Tyr-Val-His-Pro-Ala-OH
Succinyl-Arg-Val-Tyr-Val-His-Pro-Ala-OH
Asp-Arg-Val-Tyr-Val-His-Pro-Ala-OH
Asn-Arg-Val-Tyr-Val-His-Pro-Ala-OH
Asn-Arg-Val-Tyr-Val-His-Pro-Leu-OH
Asn-Arg-Val-Tyr-Val-His-Pro-Gly-OH
Asn-Arg-Val-Tyr-Val-His-Pro-Ile-OH
D-Asn-Arg-Val-Tyr-Val-His-Pro-Leu-OH AII receptor inhibitory activity is disclosed in Kisfaludy et al. U.S. Pat. No. 4,179,433 for compounds of the formula $X^e$-Arg-Val-Tyr-Ile-His-Pro-$Y^e$  (I$^e$)

wherein $X^e$ is a radical derived from an aliphatic α-aminooxycarboxylic acid and $Y^e$ is a radical derived from an aliphatic α-amino-carboxylic acid.

The preferred representatives of the radicals derived from an aliphatic α-aminooxy-carboxylic acid represented by $X^e$ are aminooxyacetyl and α-aminooxy-propionyl groups, while $Y^e$ preferably represents a leucyl, isoleucyl, alanyl or threonyl group.

Acid-addition salts and complexes of the peptides having the formula I$^e$ are also within the scope of this invention.

Examples of this class of compounds include aminooxyacetyl-Arg-Val-Tyr-Ile-His-Pro-Leu-OH; and D-α-aminooxypropionyl-Arg-Val-Tyr-Ile-His-Pro-Leu-OH.

Hallinan et al. U.S. Pat. No. 4,204,991 discloses compounds having AII receptor inhibitory activity of the formula

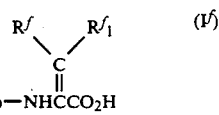

Sar—Arg—Val—Tyr—Ile—His—Pro—NHĊCO$_2$H wherein $R^f$ is hydrogen or alkyl radical containing 1–4 carbon atoms; $R_1^f$ is hydrogen or an alkyl radical containing 1–4 carbon atoms; and the stereochemical configuration of each of the optically active amino acid residues is L or DL.

See also West German Offenlegungschrift No. 2846200 (Chemical Abstracts, Vol. 91, Abstract No. 74989d) below.

Examples include

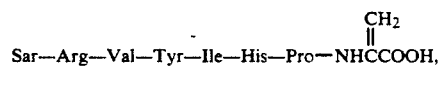

Sar—Arg—Val—Tyr—Ile—His—Pro—NHĊCOOH,

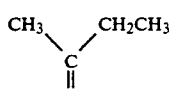

Sar—Arg—Val—Tyr—Ile—His—Pro—NHĊCOOH, and

Sar—Arg—Val—Tyr—Ile—His—Pro—NHĊCOOH .

Kisfaludy et al. U.S. Pat. No. 4,209,442 discloses as having AII receptor inhibitory activity compounds of the formula $X^g$-Arg-Val-Tyr-Ile-His-Pro-$Y^g$  (I$^g$)

wherein $X^g$ is a radical derived from an aliphatic α-hydroxycarboxylic acid and $Y^g$ is a radical derived from an aliphatic α-amino carboxylic acid.

The preferred representatives of the radicals derived from an aliphatic α-hydroxy-carboxylic acid represented by $X^g$ are hydroxyacetyl and α-hydroxypropionyl groups, while $Y^g$ preferably represents a leucyl, isoleucyl, alanyl or threonyl group.

Examples include hydroxyacetyl-Arg-Val-Tyr-Ile-His-Pro-Leu-OH,
hydroxyacetyl-Arg-Val-Tyr-Ile-His-Pro-Ile-OH,
hydroxyacetyl-Arg-Val-Tyr-Ile-His-Pro-Ala-OH
hydroxyacetyl-Arg-Val-Tyr-Ile-His-Pro-Thr(Me)-OH,
α-hydroxypropionyl-Arg-Val-Tyr-Ile-His-Pro-Leu-OH, and α-hydroxypropionyl-Arg-Val-Tyr-Ile-His-Pro-Ile-OH.

AII receptor inhibitory compounds of the formula $$X^h\text{-Arg-Val-Tyr-Ile-His-Pro-}Y^h\text{-OA}^h \qquad (1^h)$$

are disclosed in Nyeki et al. U.S. Pat. No. 4,330,532 wherein $X^h$ stands for the acyl group of an N-methylamino acid, preferably a sarcosyl group, or the acyl group of an aliphatic α-aminooxy- or α-hydroxycarboxylic acid, $Y^h$ is the residue of an aliphatic α-hydroxycarboxylic acid, preferably a residue of lactic acid or L-2-hydroxy-3-methylvaleric acid, and $A^h$ is hydrogen or a $C_{1-5}$ alkyl group.

The acid addition salts and complexes of the above peptides are also embraced by the scope of the invention.

Examplary of compounds of this class are
Sar-Arg-Val-Tyr-Ile-His-Pro-Lac,
Sar-Arg-Val-Tyr-Ile-His-Pro-Lac(OC$_2$H$_5$), and
Sar-Arg-Val-Tyr-Ile-His-Pro-2-hydroxy-3-methylvaleric acid.

Furukawa et al. U.S. Pat. No. 4,340,598 discloses AII antagonists of the formula (1$^i$)

wherein $R^{1i}$ is lower alkyl, or phenyl-C$_{1-2}$ alkyl which may be substituted with halogen or nitro; $R^{2i}$ is lower alkyl, cycloalkyl or phenyl which may be substituted with halogen, lower alkyl, lower akoxyl or di(loweralkyl)-amino; one of $R^{3i}$ and $R^{4i}$ is of the formula: —(CH$_2$-)$_{ni}$—COR$^{5i}$ in the formula R$^{5i}$ is amino, lower alkoxyl or hydroxyl and ni is integer of 0, 1 or 2, and the other is hydrogen or halogen; provided that $R^{1i}$ is lower alkyl or phenethyl when $R^{3i}$ is halogen, ni is 1 and $R^{5i}$ is lower alkoxyl or hydroxyl, and its salts.

Examples include 1-benzyl-4-chloro-2-phenylimidazole-5-acetamide, 1-benzyl-2-n-butyl-4-chloroimidazole-5-acetamide, and 1-benzyl-2-n-butyl-5-chloroimidazole-4-acetic acid.

AII antagonists of the formula:

(1$^j$)

are disclosed in Furukawa et al. U.S. Pat. No. 4,355,040 wherein $R^{1j}$ is lower alkyl, cycloalkyl or phenyl which may be substituted with one to three groups including halogen, nitro, amino, mono(lower alkyl)amino, di(lower alkyl)amino, lower alkyl, lower alkoxy, benzyloxyl and/or hydroxyl, $X^{1j}$, $X^{2j}$ and $X^{3j}$ are each hydrogen, halogen, nitro, amino, lower alkyl, lower alkoxyl, benzyloxyl or hydroxyl; $Y^j$ is halogen and $R^{2j}$ is hydrogen or lower alkyl, provided that $X^{1j}$ is halogen, lower alkyl, lower alkoxyl, benzyloxyl or hydroxyl when $R^{1j}$ is unsubstituted or phenyl substituted only with one halogen, di(lower alkyl)amino, lower alkyl or lower alkoxyl, and its salts.

Examples include 1-(2-chlorobenzyl)-2-n-butyl-4-chloroimidazole-5-acetic acid, 1-benzyl-4-chloro-2-(4-chloro-3,5-dinitrophenyl)imidazole-5-acetic acid, 4-chloro-1-(4-methoxy-3-methylbenzyl)-2-phenylimidazole-5-acetic acid, and 4-chloro-1-(4-ethoxy-3-methylbenzyl)-2-phenyl-imidazole-5-acetic acid.

Wissmann et al. U.S. Pat. No. 4,013,791 discloses AII antagonists of the formula $$Y^k\text{-Arg-Val-Tyr-Val-His-Pro-Phegyl-OH} \qquad (1^k)$$

in which $Y^k$ stands for the sarcosyl, succinamoyl or succinoyl radical.

An example of such compounds is succinamoyl-Arg-Val-Tyr-Val-His-Pro-Phegly-OH where Phegly-OH is a L-C-phenylglycine residue.

An AII antagonist of the formula

L—(N-Methyl)-Ile—L—Arg—L—Val—L—Tyr—L—Ile—L—His—L—Pro—L—Ile
(1)            (2)      (3)     (4)      (5)       (6)       (7)     (8)

is disclosed in Bumpus et al. U.S. Pat. No. 3,923,769.

Bumpus et al. U.S. Pat. No. 3,923,770 discloses an AII antagonist of the formula

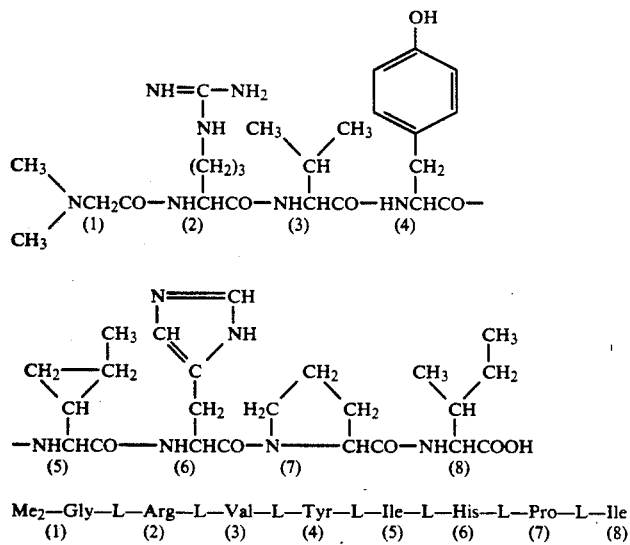
Me$_2$—Gly—L—Arg—L—Val—L—Tyr—L—Ile—L—His—L—Pro—L—Ile
 (1)     (2)    (3)    (4)    (5)   (6)    (7)    (8)
Bumpus et al. U.S. Pat. No. 3,923,771 discloses an AII antagonist of the formula
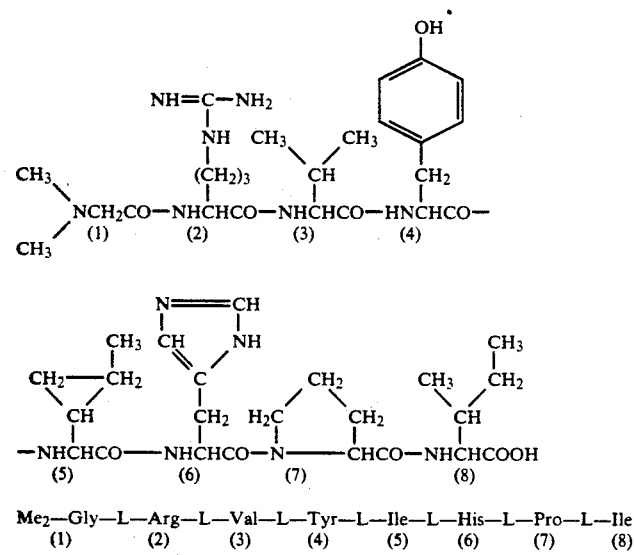
Me$_2$—Gly—L—Arg—L—Val—L—Tyr—L—Ile—L—His—L—Pro—L—Ile
 (1)     (2)    (3)    (4)    (5)   (6)    (7)    (8)
An AII antagonist of the formula
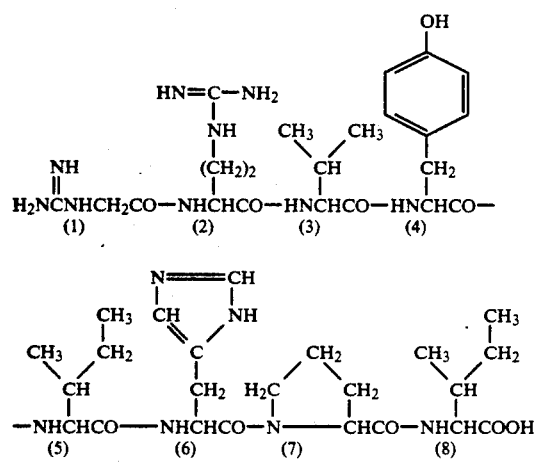

An AII antagonist of the formula

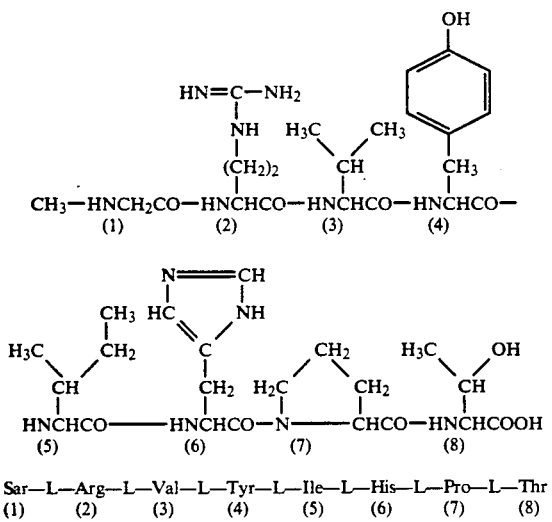

Sar—L—Arg—L—Val—L—Tyr—L—Ile—L—His—L—Pro—L—Thr
(1)   (2)   (3)   (4)   (5)   (6)   (7)   (8)

is disclosed in Bumpus et al. U.S. Pat. No. 3,925,345.

West German Offenlegungsschift No. 2520106 discloses as AII antagonists compounds of the formula

(where $R^l$ is dimethylglycyl, N-methylisoleucyl, guanidylacetyl or sarcosyl and $X^l$ is a sarcosine, O-methylsarcosine or isoleucine residue).

Bumpus et al. U.S. Pat. No. 3,976,770 discloses as having AII receptor inhibitory activity a compound of the formula

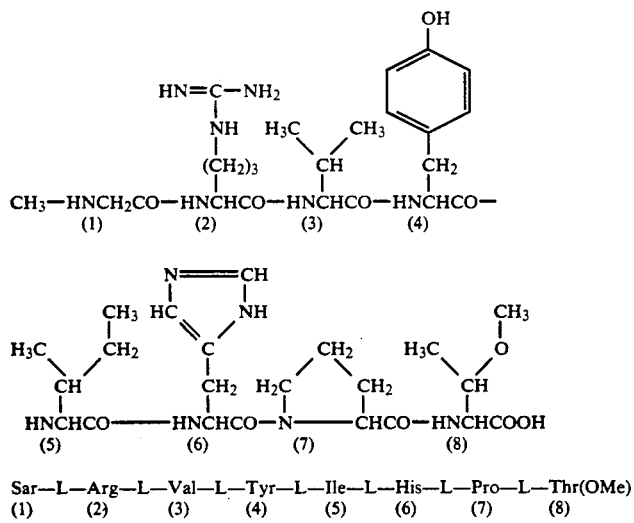

Sar—L—Arg—L—Val—L—Tyr—L—Ile—L—His—L—Pro—L—Thr(OMe)
(1)   (2)   (3)   (4)   (5)   (6)   (7)   (8)

An AII receptor blocker of the formula Sar-Arg-Val-Tyr-Val-His-Pro-OH is disclosed in Wille U.S. Pat. No. 3,915,948.

Soviet Union Patent Publication No. 891,648 discloses as an AII antagonist a compound of the formula Sar-Arg-aza-α'-Hva-Tyr-Val-His-Pro-Ile where aza-α'-Hva is aza-alpha'-homo-L-valine.

Soviet Union Patent Publication No. 687,794 (*Chemical Abstracts*, Vol 95, Abstract No. 175775v) discloses as an AII antagonist a compound of the formula Asn-Arg-aza-α-homo-Val-Tyr-Val-His-Pro-Phe-OH.

Japanese Kokai 78 23969 (*Chemical Abstracts*, Vol. 89, Abstract No. 24819n) discloses as AII antagonists compounds of the formula $R^m$-Arg-Val-Tyr-Ile-His-Pro-MeDop-OH wherein $R^m$ is H, H-Asp or $CH_3NHCH_2CO$; and MeDop is an L-α-methyldopa residue.

West German Offenlegungsschrift No. 2831271 (*Chemical Abstracts*, Vol. 91, Abstract No. 39880r) discloses compounds of the formula $HOCHR^nCO$-Arg-Val-Tyr-Ile-His-Pro-$X^n$-OH as having AII receptor inhibitory activity, wherein $R^n$ is H is $CH_3$; and $X^n$ is Leu, Ile, Ala, or Thr.

West German Offenlegungsschrift No. 2846200 (*Chemical Abstracts*, Vol. 91, Abstract No. 74909d) discloses as AII antagonists compounds of the formula

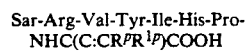

wherein $R^p$ is H, $C_1$ to $C_8$ alkyl or phenyl; and $R^{1p}$ is H or $C_1$ to $C_8$ alkyl.

East German Patent Publication No. 140,877 (*Chemical Abstracts*, Vol. 95, Abstract No. 7777d) discloses compounds of the formula

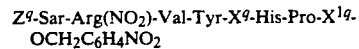

as AII antagonists, wherein $Z^q$ is phenyl-$CH_2O_2C$—; $X^q$ is Val or Ile; and $X^{1q}$ is Ile, Ala, Leu, Thr(Me) or Thr.

The above descriptions on pages 5-17 inclusive hereof of classes of AII antagonists for use in the present invention were taken from the noted patents and publications or from abstracts thereof. Reference should be made to such patents and publications themselves for their full disclosures of such classes and specific compounds within such classes, such patents and publications being incorporated herein by reference for such purposes, and as to any typographical errors or the like which may have occurred in transcription. Also, in describing such AII antagonists the superscript letters a–q (the letter "o" having been omitted) were included to distinguish among the various classes of compounds and the variable substituent groups thereof.

It is believed that any AII antagonist will possess the novel utility described herein; however, for purposes of the present invention the preferred AII antagonists are compounds which are capable of inhibiting the action of AII by at least 50% at a concentration of 1 μM or less, and especially preferred AII antagonists are compounds which are capable of inhibiting the action of AII by at least 50% at a concentration of 10 nM or less, when tested by the following standard methods. Suitable in vitro methods to determine inhibition of AII receptor activation include the Rat Isolated Stomach Strip Method described in U.S. Pat. No. 3,907,762 and by Regoli et. al, *Brit. J. Pharmacol.* 23, 351 (1964), the Rabbit Aortic Strip Method described in *Circ. Res.* XXIX: 664 (1971), and the Rat Uterine Horn Contraction method described in U.S. Pat. No. 4,204,991.

Many AII antagonists are known in the art and may be prepared by known methods or by variations thereof. Certain AII antagonists employed in the invention may exist in isomeric form. The invention contemplates all such isomers both in pure form and admixture, including racemic mixtures and their pharmaceutically acceptable salts.

The pharmaceutical compositions of the invention are administered in the form of ophthalmic pharmaceutical compositions adapted for topical administration to the eye, such as solutions, suspensions, ointments and solid inserts. Formulations of the invention may contain the AII antagonist in an amount of from about 0.0001 to about 0.1 (w/v %) and especially about 0.0001 to about 0.01 of medicament. As a unit dosage form, an amount of AII antagonist from between about 50 ng to about 0.05 mg, preferably 50 ng to 5 μg of the active substance is applied to the human eye.

Where utilized herein, the term "controlling the elevated intraocular pressure" means the regulation, attenuation and modulation of increased intraocular tension, e.g., the primary diagnostic sympton of the disease glaucoma. The term also means that the diminution, in the otherwise elevated intraocular pressure, obtained by the practice of the invention is maintained for a significant period of time as, for example, between consecutive doses of the composition of the invention.

The AII antagonists may be employed in the composition and methods of the invention as the sole IOP lowering ingredient or may be used in combination with other mechanistically distinct IOP lowering ingredients such as beta-adrenergic blocking agents, (e.g., timolol). For purposes of the present invention, the term beta-adrenergic blocker means a compound which by binding to beta-adrenergic plasma membrane receptors reduces or eliminates sympathetic activity or blocks the effects of exogenously administered catecholamines or adrenergic drugs. See, for example, Weiner, N., Drugs That Inhibit Adrenergic Nerves and Block Adrenergic Receptors, in *The Pharmaceutical Basis of Therapeutics* (ed. A. G. Goodman, L. S. Goodman, A. Gilman), Macmillan Publishing, New York, 1980, 6th ed., pp. 188–197.

Examples of preferred beta adrenergic blockers are atenolol (4-[2-hydroxy-3-[(1-methylethyl)amino]-propoxy]benzeneacetamide), metoprolol (1-[4-(2-methoxyethyl)phenoxy]-3-[(1-methylethyl)amino]-2-propanol), nadolol (5-[3-[(1,1-dimethylethyl)amino]-2-hydroxypropoxy]-1,2,3,4-tetrahydro-2,3-naphthalenediol), pindolol (1-(1H-indol-4-yloxy)-3-[(1-methylethyl)amino]-2-propanol), propranolol (1-[(1-methylethyl)amino]-3-(1-naphthalenyloxy)-2-propanol), timolol (1-[(1,1-dimethylethyl)amino]-3-[(4-morpholinyl-1,2,5-thiadiazol-3-yl)oxy]-2-propanol), labetalol (2-hydroxy-5-[1-hydroxy-2-[(1-methyl-3-phenylpropyl)amino]ethyl]-benzamide), betaxolol (1-[4-[2-(cyclopropylmethoxy)ethyl]-phenoxy]-3-[(methylethyl)amino]-2-propanol), carteolol (5-[3-[(1,1-dimethylethyl)amino]-2-hydroxypropoxy]-3,4-dihydro-2(1H)-quinolinone), bunolol (5-[3-(1,1-dimethylethyl)amino-2-hydroxypropoxy]-3,4-dihydro-1(2H)-naphthalenone), and dilevalol ([R-(R,R)]-2-hydroxy-5-[1-hydroxy-2-[(1-methyl-3-phenylpropyl)amino]ethyl]-benzamide 4-methylbenzenesulfonate salt), and pharmaceutically acceptable salts and isomers thereof.

The usefulness of beta-adrenergic blockers for lowering intraocular pressure is known in the art. Thus, the beta-adrenergic blocker timolol, is currently approved by the U.S. Food and Drug Administration for topical use as a treatment for glaucoma. It is marketed in two dose strengths, i.e., 0.25% and 0.5%. As previously stated, this agent must be used with caution in a defined patient population because of recognized untoward side effects (see Physicians Desk Reference for Ophthalmology, 11th edition, 1983, p. 126, Medical Economics Co. Inc., Oradell, N.J. 07649).

As one aspect of the present invention, it is contemplated that a reduction in intraocular pressure equivalent to that obtained by use of a beta-blocker, e.g., the approved clinical dose of the beta-blocker timolol, may be obtained by use of a lower dose of beta-blocker when such lower dose is combined with an effective amount of an AII antagonist in accordance with the present invention. It is anticipated that the use of the diminished dosage of beta-blocker, e.g., timolol, will result in a reduction of severity and frequency of timolol-like related side effects.

For purposes of this combination treatment modality, the beta-blocker and AII antagonist are preferably administered simultaneously as one composition in one pharmaceutical dosage form, but they may be applied as separate topical compositions, if desired. When applied as part of a composition including an AII antagonist, the beta-adrenergic blocker may comprise from about 0.5 μg to about 500 μg of the composition of the invention. The preferred ranges of the components in the composition of the invention in unit dosage form are as follows:

Beta adrenergic blocker: from 5 μg to 250 μg
AII antagonist: from 50 ng to 5 μg.

When applied in separate compositions the beta-adrenergic blocking agent and the AII antagonist may be employed in such compositions in the same ranges. The individual dosage requirements, i.e., the amount of each dose and the frequency of administration, may vary depending on the severity of the disease and the response of the patient.

Since the compositions of the invention and the composition including the beta-adrenergic blocker can be administered separately, the invention also relates to combining separate pharmaceutical compositions in kit form, that is, combining two separate units, an inventive pharmaceutical composition and a topical pharmaceutical composition including a beta-adrenergic blocker in a single package. A particular advantage of the kit resides in the ability to provide a combination of an inventive composition which can be administered once or twice a day and a topical beta-adrenergic blocker composition which may be administered as necessary or desired.

Those skilled in the art will appreciate that the "intraocular pressure reducing concentration" for such combination therapy will consist of a range of concentrations (doses), and that there will be a lower limit to said concentration below which, the present invention will not operate. For purposes of this invention, this lower limit or minimum dosage may be considered to be about 5% of the effective dose (threshold dose) of the particular component. The intraocular pressure reducing concentration that is actually utilized, whether for an AII antagonist or for a particular beta-adrenergic blocker, will depend on, inter alia, the potency of each particular material, the combination being administered and the age, size and condition of the patient being treated as well as on the severity of the disease state.

I also contemplate that the elevation in IOP associated with the clinical ophthalmic and systemic use of anti-inflammatory steroids can be reduced by the administration of an AII antagonist. In particular, an increase in IOP is most often associated with the administration of steroidal anti-inflammatory agents. Anti-inflammatory steroids include hydrocortisone, cortisone, prednisolone, prednisone, dexamethasone, methylprednisolone, triamcinolone, betamethasone, alclometasone, flunisolide, beclomethasone, clorocortolone, diflorasone, halcinonide, fluocinonide, flucinolone, desoximetasone, medrysone, paramethasone, 9,21-dichloro-17-[(2-furanylcarbonyl)oxy]-11-hydroxy-16α-methyl-pregna-1,4-diene-3,20-dione and fluorometholone, and their pharmaceutically acceptable salts and esters. Preferred steroids are hydrocortisone, prednisolone, dexamethasone, betamethasone, beclomethasone, medrysone and fluoromethalone and their pharmaceutically acceptable salts and esters. This rise in IOP may occur with all modes of administration of the drugs, including systemic (usually oral), local injection (e.g., depot injection), and especially with ophthalmic topical or intravitreal administration. The AII antagonist may be administered following steroid treatment to lower elevated IOP, or may be co-administered with the steroid to suppress the IOP-raising effect of the steroid while not interfering with the anti-inflammatory activity of the steroid.

It is further contemplated that any possible combination of dosage forms may be used to administer the combination, e.g., oral steroid/topical AII antagonist, topical steroid/topical AII antagonist, and locally injected steroid/topical AII antagonist, although a preferred combination comprises a steroid and a topical AII antagonist. For ophthalmic use, a combination of a topical steroid and a topical AII antagonist is preferred. More preferred is a topical ophthalmic pharmaceutical dosage form comprising both a steroid and an AII antagonist. Such compositions or combinations can be employed in a method for reducing and controlling the elevated IOP associated with ophthalmic and systemic use of steroidal anti-inflammatory agents, which method comprises administering to a mammal effective amounts of a steroid and an AII antagonist, either separately or in the same pharmaceutical composition.

Since the present invention relates to treatment with a combination of an AII antagonist and a steroidal anti-inflammatory agent wherein the AII antagonist and steroid may be administered separately, the invention also relates to combining separate pharmaceutical compositions in kit form, that is, combining two separate units, an AII antagonist pharmaceutical composition and a steroid pharmaceutical composition, in a single package. Preferred components of the kit comprise a topical ophthamological AII antagonist pharmaceutical composition and a pharmaceutically acceptable steroid composition. More preferred components of the kit are a topical ophthamological AII antagonist pharmaceutical composition and a topical ophthamological steroid pharmaceutical composition. A particular advantage of the more preferred embodiment of the kit resides in the ability to provide a combination of an AII antagonist composition which can be administered once or twice a day and a steroid composition which may be administered as frequently as once each hour.

In this combination treatment modality, topical formulations of the invention may combine the following amounts of each AII antagonist and steroidal constituent, or each constituent may be administered separately:

AII antagonist from about 0.0001 to about 0.1 (w/v %) and especially about 0.0001 to about 0.01% of medicament. As a unit dosage form, an amount of AII antagonist from between about 50 ng to about 0.05 mg, preferably about 50 ng to about 5 $\mu$g of the active component is applied to the human eye. Individual dosage requirements, i.e., the amount of each dose and the frequency of administration, will depend on the potency of the particular AII antagonist, the severity of the increase in IOP and the response of the patient.

Steroid from about 0.05 to about 1.5 (w/v %) of medicament. As a unit dosage form, an amount of steroid from between 20 $\mu$g to 600 $\mu$g of the active composition is applied to the human eye. Individual dosage requirements, i.e., the amount of each dose and the frequency of administration will depend on the potency of the particular steroid, the severity of the disease and the response of the patient. Approximate ranges for such steroids are well known to those skilled in the art. The particular steroid selected will determine which AII antagonist and concentration thereof to select for use in a combination preparation.

In one embodiment of the invention, both active ingredients, i.e., AII antagonist and steroid, will be administered simultaneously and be contained in one pharmaceutical dosage form, each component being present in the dosage form in its own respective preferred concentration. When the steroid is administered systemically or topically other than in an ophthalmological composition, the concentration of the steroid in the composition and the unit dosage weight may vary considerably, depending as above on such factors as the potency of the steroid, its onset and duration of action as well as the severity of the disease, and the response of the patient. Appropriate dosage ranges for systemic and topical administration of each steroid are well known in the art.

Those skilled in the art will know that for solutions and suspensions, a particular dosage of active ingredient may be calculated if one assumes that one drop of solution is being administered and if one knows the concentration (w/v) of the particular solution that is being administered. Thus, one drop (1/20 ml) of a 0.25% solution (contains 2.5 mg of active per ml) is known to contain 0.125 mg or 125 $\mu$g of active.

The IOP-lowering effects of the compositions employed in the invention may be measured by the procedure described by Watkins et al., *J. Ocular Pharmacol.* 1 (2):161–168, 1985.

To prepare suitable dosage forms, the active compositions may be conveniently admixed with a non-toxic pharmaceutically acceptable carrier suitable for topical ophthalmolgic administration. Typical of such pharmaceutically acceptable carriers are, for example, water, mixtures of water and water-miscible solvents such as lower alkanols or vegetable oils, petroleum based jelly, and including also from 0.5 to 5% by weight of hydroxyethyl cellulose, ethyl oleate, carboxymethyl cellulose, polyvinylpyrrolidone, and other water soluble ophthalmologically acceptable non-toxic polymers, for example, cellulose derivatives such as methyl cellulose, alkali metal carboxymethyl cellulose, hydroxyethyl cellulose, hydroxypropyl cellulose, hydroxypropylmethyl cellulose; acrylates such as polyacrylic acids salts; ethylacrylates; polyacrylamides; natural products such as gelatin, alginates, pectins, tragacanth, karaya, chondrus, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, neutralized carbopol and xanthan gum; and mixtures of these polymers. The pharmaceutical preparation may also contain non-toxic auxiliary substances such as emulsifying, preserving, wetting, bodying agents and the like, as for example, polyethylene glycols 200, 300, 400 and 600; carbowaxes 1,000, 1,500, 4,000, 6,000 and 10,000; antibacterial components such as quarternary ammonium compounds; phenylmercuric salts known to have cold sterilizing properties and which are non-injurious in use; thimerosal; methyl and propyl paraben; benzyl alcohol; phenyl ethanol; buffering ingredients such as alkali metal chloride, borate, acetate, gluconate buffers; antioxidants such as sodium metabisulfite, butylated hydroxyanisol (BHA), butylated hydroxytoluene (BHT) and the like; and other conventional ingredients such as sorbitan monolaurate, triethanolamineoleate, polyoxyethylene sorbitan monopalmitylate, dioctyl alkali metal sulfosuccinate, monothioglycerol, ethylenediamine tetracetic acid and the like.

Additionally, suitable ophthalmic vehicles can be used as carrier media for the present purpose including conventional phosphate buffer vehicle systems, isotonic boric acid vehicles, isotonic alkaki chloride vehicles, tris and the like.

The pharmaceutical preparation may also be in the form of a solid insert. For example, one may use a solid water soluble polymer as the carrier for the medicament. Inserts that are known in the art that are suitable for this use include those described in British Patent 15611, and in U.S. Pat. Nos. 3,993,071; 3,986,510; 3,868,445; and 3,867,510. Solid water insoluble inserts, such as those prepared from ethylene vinyl acetate copolymer, may also be utilized.

The compositions of the invention may include additional therapeutic agents in addition to the AII antagonist. For example antibiotics, anesthetics as well as other IOP-lowering agents may be present.

The following examples are intended to illustrate, but not to limit, the present invention. In such examples, Compound A refers to saralasin. It is contemplated, however, that therapeutically effective amounts of other AII antagonists as discussed above may be substituted in its place.

EXAMPLE 1

| Topical Solution: | |
|---|---|
| Ingredients | mg/ml |
| Compound A | 1.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sterile Water | q.s. ad 1.0 mL |
| 1.ON NaOH | q.s. ad pH 7.4 |

Mix the ingredients under sterile conditions and using standard techniques to obtain the ophthamological solution.

EXAMPLE 2

| Topical Solution: | |
|---|---|
| Ingredients | mg/ml |
| Compound A | 1.0 |
| Timolol | 5.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sterile Water | q.s. ad 1.0 mL |
| 1.ON NaOH | q.s. ad pH 7.4 |

Mix the ingredients under sterile conditions and using standard techniques to obtain the ophthamological solution.

EXAMPLE 3

| Topical Solution: | |
|---|---|
| Ingredients | mg/ml |
| Compound A | 1.0 |
| Dexamethasone Sodium Phosphate | 1.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sterile Water | q.s. ad 1 mL |
| 1.ON NaOH | q.s. ad pH 7.4 |

Mix the ingredients under sterile conditions and using standard techniques to obtain the ophthamological solution.

Again, other AII antagonists, steroids and/or beta-adrenergic blocking agent can be employed in place of those listed in the formulations above, with the particular amounts varying depending on the drugs employed.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

I claim:

1. A method for reducing elevated intraocular pressure in a mammal which comprises topically administering to an eye of said mammal an intraocular pressure reducing amount of angiotensin II receptor blocker.

2. A method according to claim 1 wherein the angiotensin II receptor blocker is administered as a composition comprising said angiotensin II receptor blocker and an ophthamologically acceptable carrier for topical use.

3. A method according to claim 1 wherein the angiotensin II receptor blocker is a compound of the formula Sar$^1$ Ala$^8$,
Sar$^1$ Ile$^8$,
Succ$^1$ Val$^5$ Phenylgly$^8$,
desAsp$^1$ Ile$^8$,
Sar$^1$ Thr$^8$,
Sar$^1$ Cys-Me$^8$,
Sar$^1$ Tyr-Me$^4$,
Gly$^8$,
Ile$^8$,
Leu$^8$,
Sar$^1$ Leu$^8$,
desAsp$^1$ Leu$^8$,
Sar$^1$ Me-Ala$^7$ Ile$^8$,
Sar$^1$ DL-Nipecotamide$^7$ Ile$^8$,
Sar$^1$ Sar$^7$ Ile$^8$,
8-L-Ala,
Met$^8$,
Thr$^8$,
O-Me Thr$^8$,
N-Me Ile$^8$,
N-Me Phe$^8$,
Sar$^1$ Sar$^7$ Leu$^8$,
Sar$^1$ Sar$^7$ Thr(Me)$^8$,
Sar$^1$ Sar$^7$ DLaIle$^8$,
MeIle$^1$ Thr$^8$,
Me$_2$Gly$^1$ Thr$^8$,
GdnAc$^1$ Thr$^8$,
desAsp$^1$ Thr$^8$,
Sar$^1$ Ser(Me)$^8$,
Sar$^1$ Thr$^8$,
Sar$^1$ Thr(Me)$^8$,
MeAspNH$_2$$^1$ Ile$^8$,
Sar$^1$ MeTyr$^4$ Ile$^8$,
Sar$^1$ MeIle$^5$ Ile$^8$,
Sar$^1$ MeIle$^8$,
Sar$^1$ MeIle$^5$ MeIle$^8$,
Sar$^1$ Thr (O-$\beta$-Me)$^8$,
Sar$^1$ Met$^8$,
Sar$^1$ Ser$^8$,
Ile$^5$ Ala$^8$,
Ile$^5$,8-(3-amino-4-phenyl)butyric acid,
Asn$^1$ Ala$^8$,
Sar$^1$ Cys(Me)$^8$,
Phe$^4$ Tyr$^8$,
OctanoylLeu$^8$,
Cys$^8$,
Phe$^4$ Tyr$^8$,
desAsp$^1$ Phe$^4$ Tyr$^8$,
para-fluoroPhe$^4$ or
para-fluoroPhe$^8$ wherein the abbreviations indicate substitutions in the angiotensin II sequence Asp-Arg-Val-Tyr-Ile-His-Pro-Phe at the location identified by the superscript.

4. A method according to claim 1 wherein the Angiotensin II receptor blocker is a compound of the formula

```
 1    2    3   4    5   6    7   8
Asp—Arg—Val—Tyr—Ile—His—Pro—R^b
``` wherein

R$^b$ is Leu (leucine),
Ile (isoleucine),
Val (valine), or
α-amino-n-But (α-amino-n-butyric acid) and Asp is aspartyl, Arg is Arginyl, Val is valyl, Tyr is tyrosyl, Ile is isoleucyl, His is histidyl and Pro is prolyl.

5. A method according to claim 1 wherein the Angiotensin II receptor blocker is a compound of the formula X$^c$-Arg-Val-Tyr-Ile-His-Pro-Y$^c$-OA$^c$    (I$^c$)

wherein
X$^c$ stands for the acyl group of an N-methylamino acid, or the acyl group of an aliphatic α-hydroxy- or α-aminooxycarboxylic acid,
Y$^c$ is the residue of an aliphatic amino acid, and
A$^c$ is a C$_{1-5}$ alkyl group.

6. A method according to claim 1 wherein the Angiotensin II receptor blocker is a compound of the formula X$^e$-Arg-Val-Tyr-Ile-His-Pro-Y$^e$    (I$^e$)

wherein
X$^e$ is a radical derived from an aliphatic α-aminooxycarboxylic acid and
Y$^e$ is a radical derived from an aliphatic α-aminocarboxylic acid.

7. A method according to claim 1 wherein the Angiotensin II receptor blocker is a compound of the formula wherein R$^f$ is hydrogen or alkyl radical containing 1–4 carbon atoms; R$^f_1$ is hydrogen or an alkyl radical containing 1–4 carbon atoms.

8. A method according to claim 1 wherein the Angiotensin II receptor blocker is a compound of the formula X$^g$-Arg-Val-Tyr-Ile-His-Pro-Y$^g$    (I$^g$)

wherein
X$^g$ is a radical derived from an aliphatic α-hydroxycarboxylic acid and
Y$^g$ is a radical derived from an aliphatic α-amino carboxylic acid.

9. A method according to claim 1 wherein the Angiotensin II receptor blocker is a compound of the formula X$^h$-Arg-Val-Tyr-Ile-His-Pro-Y$^h$-OA$^h$    (I$^h$)

wherein
X$^h$ stands for the acyl group of an N-methylamino acid, or the acyl group of an aliphatic α-aminooxy- or α-hydroxycarboxylic acid,
Y$^h$ is the residue of an aliphatic α-hydroxycarboxylic acid, and
A$^h$ is hydrogen or a C$_{1-5}$ alkyl group.

10. A method according to claim 1 wherein the Angiotensin II receptor blocker is a compound of the formula

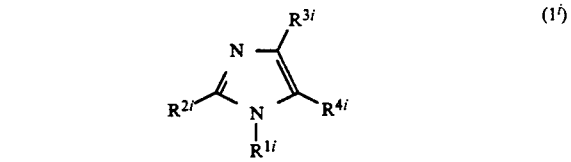

(I$^i$)

wherein R$^{1i}$ is lower alkyl, or phenyl-C$_{1-2}$alkyl which may be substituted with halogen or nitro; R$^{2i}$ is lower alkyl, cycloalkyl or phenyl which may be substituted with halogen, lower alkyl, lower alkoxyl or di(-loweralkyl)-amino; one of $R^{3i}$ and $R^{4i}$ is of the formula: $-(CH_2)_{ni}-COR^{5i}$ in the formula $R^{5i}$ is amino, lower alkoxyl or hydroxyl and ni is integer of 0, 1 or 2, and the other is hydrogen or halogen; provided that $R^{1i}$ is lower alkyl or phenethyl when $R^{3i}$ is halogen, ni is 1 and $R^{5i}$ is lower alkoxyl or hydroxyl, and its salts.

11. A method according to claim 1 wherein the Angiotensin II receptor blocker is a compound of the formula

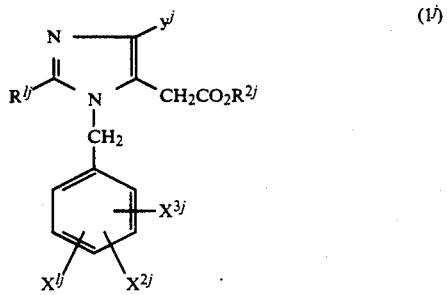

(1$^j$)

wherein $R^{1j}$ is lower alkyl, cycloalkyl or phenyl which may be substituted with one to three groups including halogen, nitro, amino, mono(lower alkyl)amino, di(-lower alkyl)amino, lower alkyl, lower alkoxyl, benzyloxyl and/or hydroxyl, $X^{1j}$, $X^{2j}$ and $X^{3j}$ are each hydrogen, halogen, nitro, amino, lower alkyl, lower alkoxyl, benzyloxyl or hydroxyl; $Y^j$ is halogen and $R^{2j}$ is hydrogen or lower alkyl, provided that $X^{1j}$ is halogen, lower alkyl, lower alkoxyl, benzyloxyl or hydroxyl when $R^{1j}$ is unsubstituted or phenyl substituted only with one halogen, di(lower alkyl)amino, lower alkyl or lower alkoxyl, and its salts.

12. A method according to claim 1 wherein the Angiotensin II receptor blocker is a compound of the formula

(I$^k$)

in which $Y^k$ stands for the sarcosyl, succinamoyl or succinoyl radical.

13. A method according to claim 1 wherein the Angiotensin II receptor blocker is a compound of the formula

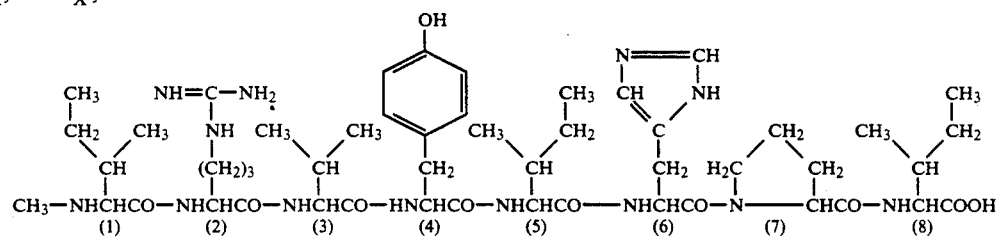

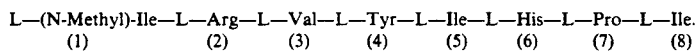

14. A method according to claim 1 wherein the Angiotensin II receptor blocker is a compound of the formula

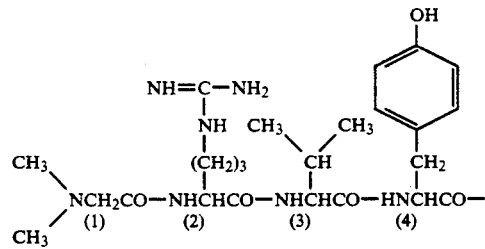

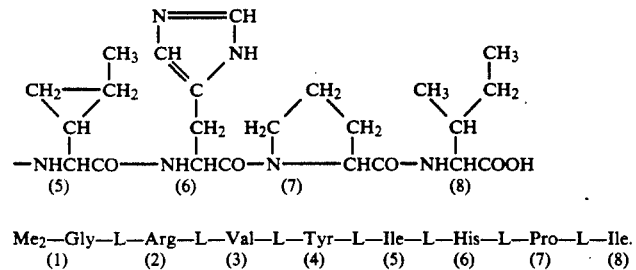

15. A method according to claim 1 wherein the Angiotensin II receptor blocker is a compound of the formula

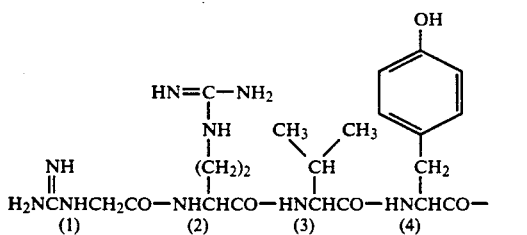
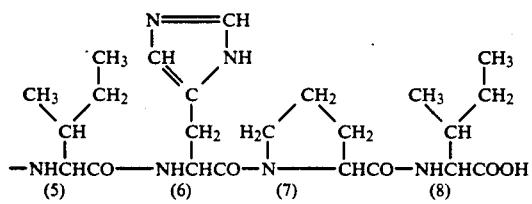
GuaAc—L—Arg—L—Val—L—Tyr—L—Ile—L—His—L—Pro—L—Ile.
(1)   (2)   (3)   (4)   (5)   (6)   (7)   (8)
16. A method according to claim 1 wherein the Angiotensin II receptor blocker is a compound of the formula
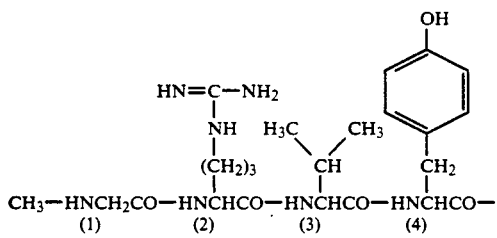
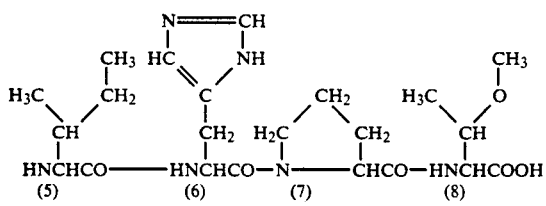
Sar—L—Arg—L—Val—L—Tyr—L—Ile—L—His—L—Pro—L—Thr(OMe).
(1)   (2)   (3)   (4)   (5)   (6)   (7)   (8)
17. A method according to claim 1 wherein the Angiotensin II receptor blocker is a compound of the formula
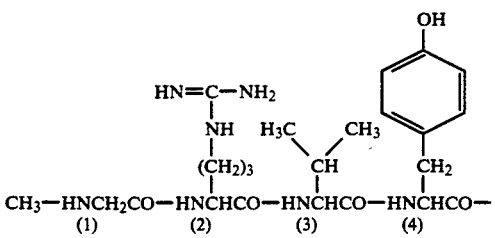
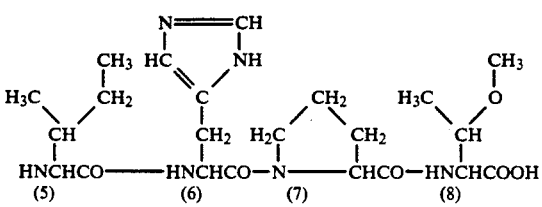

Sar—L—Arg—L—Val—L—Tyr—L—Ile—L—His—L—Pro—L—Thr(OMe).
(1)   (2)   (3)   (4)   (5)   (6)   (7)   (8)

18. A method according to claim 1 wherein the Angiotensin II receptor blocker is a compound of the formula $$R^l\text{-L-Arg-L-Val-L-Tyr-L-Ile-L-His-L-Pro-L-}X^l \quad (I)$$

(where $R^l$ is dimethylglycyl, N-methylisoleucyl, guanidylacetyl or sarcosyl and $X^l$ is a sarcosine, O-methylsarcosine or isoleucine residue).

19. A method according to claim 1 wherein the Angiotensin II receptor blocker is a compound of the formula Sar-Arg-Val-Try-Val-His-Pro-OH, Sar-Arg-aza-α'-Hva-Try-Val-His-Pro-Ile-OH, or Asn-Arg-aza-α-homo-Val-Tyr-Val-His-Pro-Phe-OH, wherein aza-α'-Hva is aza-alpha'-homo-L-valine.

20. A method according to claim 1 wherein the Angiotensin II receptor blocker is a compound of the formula $R^m$-Arg-Val-Tyr-Ile-His-Pro-MeDop-OH wherein $R^m$ is H, H-Asp or $CH_3NHCH_2CO$; and MeDop is an L-α-methyldopa residue.

21. A method according to claim 1 wherein the Angiotensin II receptor blocker is a compound of the formula HOCHR$^n$CO-Arg-Val-Tyr-Ile-His-Pro-X$^n$-OH wherein R$^n$ is H is $CH_3$; and X$^n$ is Leu, Ile, Ala, or Thr.

22. A method according to claim 1 wherein the Angiotensin II receptor blocker is a compound of the formula Z$^q$-Sar-Arg(NO$_2$)-Val-Tyr-X$^q$-His-Pro-X$^{1q}$-OCH$_2$C$_6$H$_4$NO$_2$ wherein Z$^q$ is phenyl-CH$_2$O$_2$C—; X$^q$ is Val or Ile; and X$^{1q}$ is Ile, Ala, Leu, Thr(Me) or Thr.

23. A kit comprising in separate containers in a single package pharmaceutical compositions for use in combination to reduce and control elevated intraocular pressure, which comprises in one container a pharmaceutical composition comprising an intraocular pressure reducing amount of an angiotensin II receptor blocker in a topical ophthamological carrier and in a second container a pharmaceutical composition comprising an intraocular pressure reducing amount of a beta-adrenergic blocking agent in a topical ophthamological carrier.

24. A kit comprising in separate containers in a single package pharmaceutical compositions for use in combination to reduce and control the elevated intraocular pressure associated with the use of steroidal anti-inflammatory agents in humans, which comprises in one container a pharmaceutical composition comprising an intraocular pressure reducing amount of an angiotension receptor blocker and in a second container, a pharmaceutical composition comprising an anti-inflammatory effective amount of a steroid in a pharmaceutically acceptable carrier.

25. A kit of claim 24 wherein the steroid carrier is a topical, ophthamologically acceptable carrier.

* * * * *